United States Patent [19]

Baran et al.

[11] Patent Number: 5,233,063
[45] Date of Patent: Aug. 3, 1993

[54] METABOLITES OF PENTANEDIOIC ACID DERIVATIVES

[75] Inventors: John S. Baran, Winnetka; Harman S. Lowrie, Northbrook, both of Ill.

[73] Assignee: G. D. Searle & Co., Chicago, Ill.

[21] Appl. No.: 641,993

[22] Filed: Jan. 16, 1991

Related U.S. Application Data

[62] Division of Ser. No. 157,767, Feb. 18, 1988, Pat. No. 5,055,613.

[51] Int. Cl.$^5$ .............................................. C07B 59/00
[52] U.S. Cl. .................................. 554/213; 568/496; 568/600; 568/852
[58] Field of Search ............. 260/405.5; 562/508, 562/509, 470; 554/213; 568/496, 852, 600

[56] References Cited

U.S. PATENT DOCUMENTS

| | | | |
|---|---|---|---|
| 3,629,449 | 12/1971 | Siddiqi | 424/317 |
| 3,818,080 | 6/1974 | Baran et al. | 260/535 P |
| 3,887,616 | 6/1975 | Lannert | 260/535 P |
| 3,940,424 | 2/1976 | Lannert | 260/343.6 |

OTHER PUBLICATIONS

Chemical Abstracts, vol. 66, No. 25, 1967, p. 10695, :11525ut.
Chemical Abstracts, vol. 69, No. 13, 1968, p. 4803, 31504z.
Chemical Abstacts, vol. 93, No. 23, 1980, p. 315, 218232u.
Chemical Abstracts, vol. 109, No. 1, 1988, p. 4144, 4182c.
Chemical Abstract 101:191433e (On the Structure of Thromboxane A$_2$), 1984.
Chemical Abstract 101:210144e (Condensation of Crotonic and Tiglic Acid Dianions with Aldehydes and Ketones), 1984.
Chemical Abstract 99:194693r (Stereo Controlled Synthesis of the C(1)-C(17) Half of Boromycin), 1983.
Chemical Abstract 68:95361j (Carbene Reactions with Dimethylmalonaldehyde Derivatives), 1968.
Breslow, et al., *Cholesterol, 7-Ketocholesterol and 25-Hydroxycholesterol Uptake Studies and Effect on 3-Hydroxy-3-Methylglutaryl-Coenzyme A Reductase Activity in Human Fibroblasts*, Biochimica et Biophysica Acta, 398 (1975) 10–17.
Betteridge, et al., *Regulation of 3-hydroxy-3-methylglutarylclenzyne-A-Reductase Activity in II Hyperlipoproteinaemia*, British Medical Journal, 1975, 4, 500–502.
Brown, et al., *Suppression of 3-hydroxy-3-methylglutaryl Coenzyme A Reductase Activity and Inhibition of Growth of Human Fibroblasts by 7-ketocholesterol*, The Journal of Biological Chemistry 249, 22, 1974, 7306–7314.

*Primary Examiner*—José G. Dees
*Assistant Examiner*—Deborah D. Carr
*Attorney, Agent, or Firm*—Joy Ann Serauskas; Paul D. Matukaitis

[57] ABSTRACT

The present invention relates to pentanedioic acid derivatives. The present invention further relates to pharmaceutical compositions containing such compounds and the use of such compounds and compositions as hypolipidemic drugs.

9 Claims, No Drawings

METABOLITES OF PENTANEDIOIC ACID DERIVATIVES

This is a division of application Ser. No. 07/157,767, filed Feb. 18, 1988, now U.S. Pat. No. 5,055,613.

BACKGROUND OF THE INVENTION

The present invention provides novel compounds which are pharmacologically useful as hypolipidemic drugs (e.g., those drugs which are helpful in reducing serum levels of cholesterol). More specifically, the compounds of the present invention are orally active hypolipidemic agents which promote their cholesterol lowering effects through their ability to inhibit the activity of the enzyme β-hydroxy-β-methyl-glutaryl Co enzyme A (HMG CoA) and thus inhibit the formation of serum cholesterol. HMG CoA is a substance which controls the rate at which cholesterol is synthesized in hepatocytes (e.g., cells of mammalian liver, which are thought to be one of the two principle in vivo sources of serum cholesterol). The present invention also relates to novel pharmaceutical compositions comprising one or more of the active compounds of the invention in combination with suitable pharmaceutical carriers as well as methods of using such compounds and pharmaceutical compositions thereof in the treatment, prevention, or mitigation of hyperlipoproteinemia including specifically type II hyperlipoproteinemia, which is characterized by an excess of serum low density lipoprotein (LDL). Thus, the compounds of the instant invention are useful to inhibit sterol biosynthesis in individuals predisposed to familial type hypercholesterolemia. The significance of such compounds is widely recognized, e.g. Breslow et al., Biochim. Biophys. Acta, 398, 10 (1975); Betheridge et al., Brit. Med. J., 4,500 (1975); and Brown et al., J. Biol. Chem. 249, 7306 (1974). In addition, the compounds can be used in in vitro diagnosis (e.g. in assays for fatty acids, cholesterol, and the like).

PRIOR ART

The use of agents which lower serum cholesterol is widely recognized and described in the art as described above. U.S. Pat. No. 4,645,858 discloses certain compounds, among others, of the formula

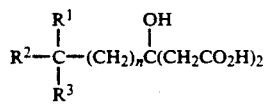

wherein $R^1$ is hydrogen or methyl; $R^2$ is methyl or ethyl; $R^3$ is methyl, or ethyl; and n is an integer from 8 to 13, inclusive. U.S. Pat. No. 3,818,080 also discloses certain compounds of this class.

SUMMARY OF THE INVENTION

The inventors believe that certain of the foregoing compounds are metabolized in vivo to the compounds of the present invention. The activity of the metabolites of the foregoing compounds has been found to be significantly greater than that of the precursor compounds.

The present invention provides compounds of the general formula I:

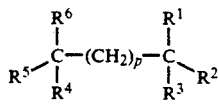

and the pharmaceutically acceptable salts thereof, wherein $R^1$, $R^2$, $R^3$ and $R^6$ are independently —H,

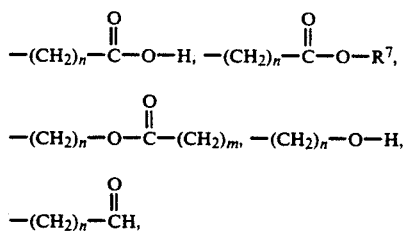

wherein $R^1$ is alkyl of from 1 to 10 carbon atoms, n and m are independent integers of from 0 to 10; wherein $R^4$ and $R^5$ are independently alkyl of from 1 to 10 carbon atoms, and p is an independent integer of from 9 to 13 carbon atoms.

The compounds and pharmaceutical compositions thereof are useful in the hypolipidemic methods of the invention.

DETAILED DESCRIPTION OF THE INVENTION

As used herein the expressions "alkyl" and "alkenyl" are defined to include straight or branched carbon-carbon linkages having the number of carbon atoms indicated. Representative alkyl moieties of any of the substituent groups include methyl, ethyl, propyl, butyl, pentyl, sec-butyl, tert-butyl, isopropyl, hexyl, heptyl, octyl, nonyl, decyl, etc. and the corresponding other isomeric forms thereof. Representative alkenyl moieties of any of the substituent groups include any of the aforementioned alkyl moieties bearing one or more degrees of unsaturation at any carbon-carbon linkage. Again, other corresponding isomeric forms are included, such as geometric isomers, diastereoisomers and enantiomers.

The compounds herein may also be prepared as addition salt forms thereof and such forms are included in the present compound formulas. Typical of such "pharmaceutically acceptable salts" are those non-toxic pharmaceutically acceptable salts such as sodium, potassium, ammonium and calcium.

Primarily representative of more preferred compounds in accordance with the present invention are those wherein the compound has the general formula II:

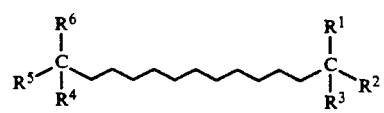

and the pharmaceutically acceptable salts thereof, wherein $R^1$, $R^2$, $R^3$ and $R^6$ are as defined above, and wherein $R^4$ and $R^5$ are independently alkyl of from 1 to 10 carbon atoms.

The especially preferred embodiments of this invention include those compounds as described above, in which $R^1$ is —OH; $R^2$ and $R^3$ are both

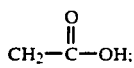

$R^6$ is —OH; $R^6$ is —CH$_2$—OH; $R^6$ is

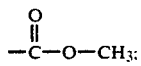

$R^6$ is

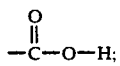

or in which $R^4$ and $R^5$ are both —CH$_3$.

Most especially preferred compounds of the present invention ar those which follow the general formula III

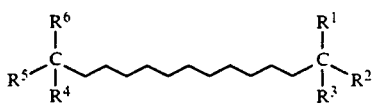

and the pharmaceutically acceptable salts thereof wherein $R^1$ is hydroxy, $R^2$ and $R^3$ are both

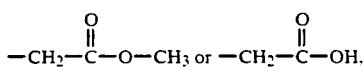

$R^4$ and $R^5$ are both methyl and $R^6$ is selected from the group consisting of hydroxy, carboxy, methoxycarbonyl, or —CH$_2$—OH, and which are:

3-(13-Hydroxy-12,12-dimethyl-tridecyl)-3-hydroxy glutaric acid;

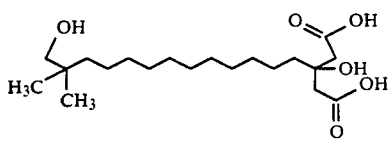

3-(12-Carbomethoxy-12-methyl-tridecyl)-3-hydroxy glutaric acid;

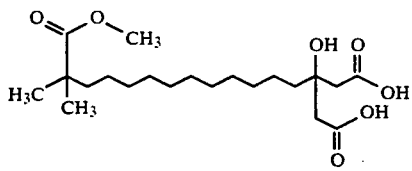

3-(12-Carboxy-12-methyl-tridecyl)-3-hydroxy glutaric acid;

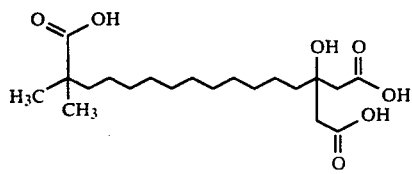

and Dimethyl 3-(12-carbomethoxy-12-methyl-tridecyl)-3-hydroxy glutarate.

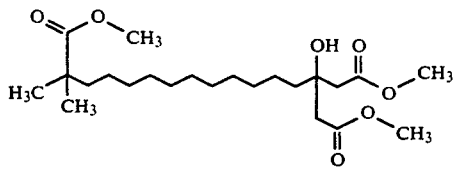

Secondly representative of preferred compounds of the present invention are those of the general Formula IV:

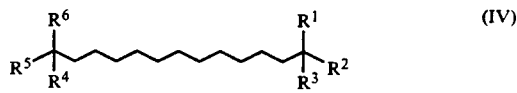

and the pharmaceutically acceptable salts thereof, wherein $R^1$ and $R^6$ are independently —H,

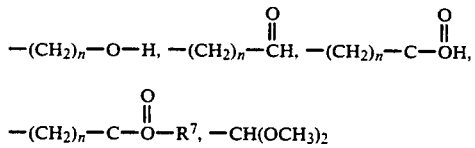

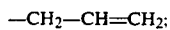

wherein $R^7$ is alkyl of from 1 to 10 carbon atoms, and n is an independent integer of from 0 to 10; wherein $R^2$ and $R^3$ are alkyl or alkenyl of from 1 to 5 carbon atoms; and wherein $R^4$ and $R^5$ are independently alkyl of from 1 to 10 carbon atoms.

Especially preferred compounds found within the general formula of IV are those wherein $R^1$ is —OH; $R^2$ and $R^3$ are both

$R^4$ and $R^5$ are both —CH$_3$; or $R^6$ is —H or —CO$_2$CH$_3$.

Most especially preferred compounds that fall within the structure of general Formula IV are
17,17-Dimethoxy-16,-16-dimethyl-4-(2-propenyl)-1-heptadecen-4-ol;

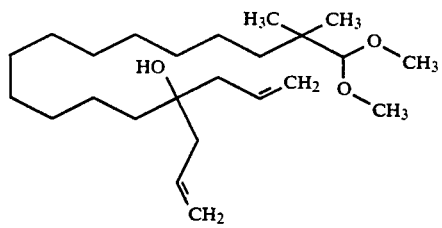

Methyl 14-hydroxy-2,2-dimethyl-14-(2-propenyl)-16-heptadecenoate

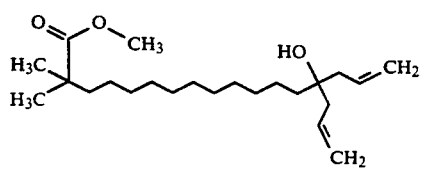

14-Hydroxy-2,2-dimethyl-14-(2-propenyl)-16-heptadecenal;

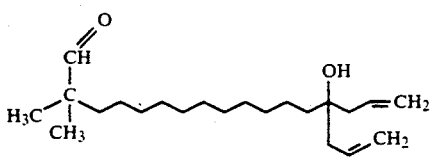

14-Hydroxy-2,2-dimethyl-14-(2-propenyl)-16-heptadecenoic acid

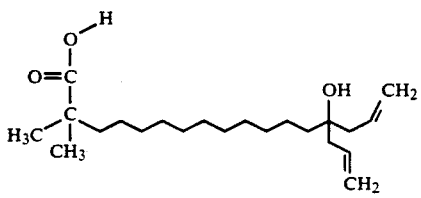

and

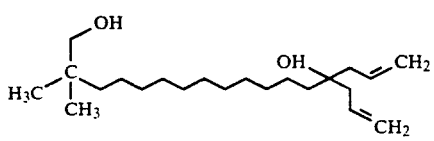

and 2,2-Dimethyl-14-(2-propenyl)-16-heptadecene-1,14-diol.

Thirdly representative of compounds of the claimed invention are those of the general Formula V

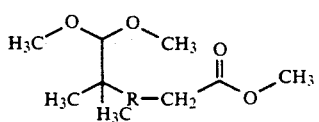

and the pharmaceutically acceptable salts thereof, wherein R is an alkane or alkene of 3 to 15 carbon atoms, with one or more degrees of unsaturation where R is alkene.

Most especially preferred compounds falling within general Formula V are those wherein R is undecane or undecene and which are namely
methyl 14, 14-dimethoxy-13, 13-dimethyl-11-tetradecenoate

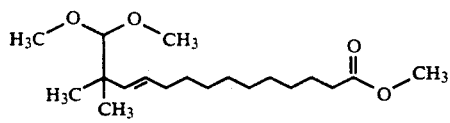

and Methyl-14,14-dimethoxy- 13,13-dimethyl tetradecanoate.

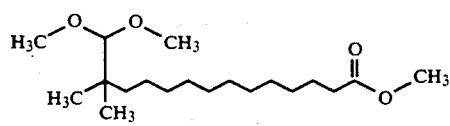

The compounds of the invention can be prepared by methods which are in themselves known, such as are described in the literature (for example Narayanan, K. S.; Berlin, K. D. J. Org. Chem. 1980, 45,2240; Johnson, P. R.; White, J. D. J. Org. Chem. 1984, 49,4424; or White, J. D.; Avery, M. A.; Choudhry, S. C.; Dhingra, O. P.; et al.; J. Am. Chem. Soc. 1983, 105,6517), namely under reaction conditions which are known and suitable for the reactions mentioned. In these reactions, it is also possible to make use of variants which are in themselves known, but are not mentioned here in greater detail. The compounds of the invention are readily prepared according to one of the following reaction schemes or modifications thereof using readily available starting materials, reagents and conventional synthesis procedures. As used herein, Ph means phenyl.

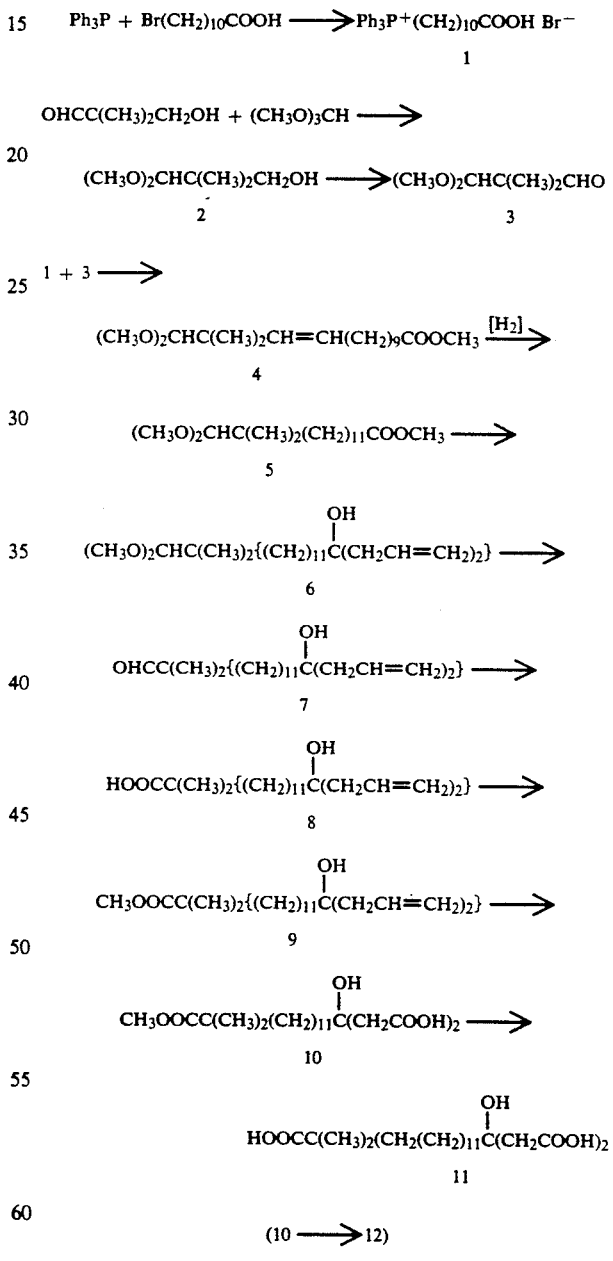

Scheme 2

-continued

1

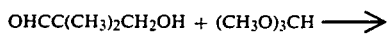

2    3

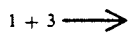

4

$(CH_3O)_2CHC(CH_3)_2(CH_2)_{11}COO(CH_3)$

5

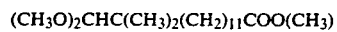

6

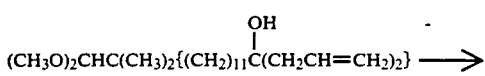

7

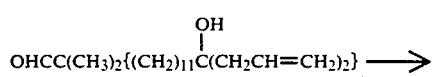

13

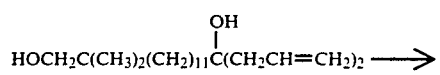

14

The compounds of the present invention can be administered in such oral dosage forms as tablets, capsules, pills, powders, granules, elixirs, tinctures, suspensions, syrups, emulsions, and suspensions. Likewise, they may also be administered in intravenous, intraperitoneal, subcutaneous, or intramuscular form, all using forms known to those of ordinary skill in the pharmaceutical arts. In general, the preferred form of administration is oral. An effective but non-toxic amount of the compound is employed in the treatment of hyperlipoproteinemias, and in particular in the treatment of Type II hyperlipidemia with resultant lowering of low density lipoproteins, and concomitant reduction in serum cholesterol levels. The dosage regimen utilizing the compounds of the present invention is selected in accordance with a variety of factors including the type. species, age, weight, sex, and medical condition of the patient; with the severity of the condition to be ameliorated, the route of administration, the renal and hepatic function of the patient, the route of administration and the particular compound employed or mixtures thereof. An ordinarily skilled veterinarian or physician can readily determine and prescribe the effective amount of the drug required to prevent, treat or arrest the progress of the condition.

Dosages of the compounds of the present invention, when used for the indicated hypolipidemic effects, will range between about 1 mg/kg/day to about 200 mg/kg/day and preferably 2.5 to 25 mg/kg/day. Advantageously, the compounds of the present invention may be administered in a single daily dose or the total daily dosage may be administered in equal divided doses of 2, 3 or 4 times daily.

In the pharmaceutical compositions and methods of the present invention, the foregoing compounds described in detail above will form the active ingredients and will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional galenical and pharmaceutical practices.

For instance, for oral administration in the form of tablets or capsules, the active drug components may be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components may be combined with any oral non-toxic pharmaceutically acceptable inert carrier such as ethanol, glycerol, water, and the like. Moreover, when desired or necessary, suitable binders, lubricants, disintegrating agents and coloring agents can also be incorporated in the mixture. Suitable binders include starch, gelatin, natural sugars such as glucose, or 8-lactose, corn sweeteners, natural and synthetic gums such acacia, tragacanth or sodium alginate, carboxymethylcellulose, polyethylene glycol, and waxes. Lubricants for use in these dosage forms include boric acid, sodium benzoate, sodium acetate, sodium chloride, and the like. Disintegraters include, without limitation, starch, methylcellulose, agar, bentonite, xanthan gum and the like.

HYPOLIPIDEMIC ACTIVITY

The compounds of this invention exhibit hypolipidemic activity as determined in the isolated hepatocyte system. The test procedures employed to measure hypolipidemic activity of the compounds of the present invention are described below.

Hepatocytes are prepared from ad lib fed rats or 48-hour fasted rats by the method of Berry and Friend (1969) with minor modifications (McCune and Harris, 1979 J. Biol. Chem. 254,10095–10101.) Lean female rats (200–300 g) are ad lib fed and on a 8:00 a.m.–8:00 p m. light cycle. The cells are isolated between 9:00–10:00 a.m., to compensate for any diurnal rhythms such as glycogen depletion.

The cells are suspended in 2 mls of Krebs-Henseleit buffer supplemented with 2% BSA (essentially fatty acid free and dialyzed) under an atmosphere of 95% $O_2$, 5% $CO_2$ in stoppered 25 ml Erlenmeyer flasks. Incubations were conducted in a shaking water bath at 37° C. for appropriate times. Cells for fatty acid and cholesterol synthesis were treated with 50 liters of $H_2O$ (10mCi/ml) after 30 minutes of pre-incubation and stopped at 60 minutes.

Assay of metabolites: Cells are terminated with $HClO_4$(0.1 ml of 60%) and treated as described previously; McCune et al., 1981 *Methods of Enzymology* 72, 557–559). The metabolites in the extracts are measured spectrophotometrically by enzymatic methods, according to the methods of Hohorst et al. (1959 Biochem. Z., 332,18–46) for pyruvate and lactate, Williamson et al. (1962) for acetoacetate and beta-hydroxybutyrate, Slein (1965) for glucose, Michal and Bergmeyer (1974) for acetyl-CoA, McCune, et al. (ibid) for glycogen. Mollering and Gruber (1966 Anal. Biochem. 17, 369 379) for citrate, and Lambrecht and Trautschold (1974 *Methods of Enzymatic Analysis*, 2101-2109) for ATP.

Determination of cholesterol and fatty acid synthesis: The rate of fatty acid synthesis and cholesterol synthesis, expressed as moles of acetate equivalents/q wet weight of hepatocytes are determined by the incorporation of $H_2O$ into total lipid, and extracted by the methods of Kates (1972 Tech. of Lipidology, 349, 363) and Harris (1975 Arch. Biochem. Biophys. 169, 168–180). Calculations are done according to Jungas (1968 Biochemistry 7, 3708–3717).

Various compounds of the present invention were added to various concentrations to the hepatocytes and incubated for a short period of time The effect of the compound was evaluated on cholesterol, fatty acid and glucose synthesis as well on other metabolites in the cell.

whose concentrations are altered, rather than simply in terms of the concentrations of the associated lipids.

Among the numerous recognized risk factors for the development of atherosclerosis, one of the best documented is the association between the concentrations of lipids in blood and the development of coronary heart disease. The evidence for the association between cholesterol concentrations in plasma and coronary heart disease is extensive and unequivocal (Task Force on Arteriosclerosis, 1977 Department of Health, Education, and Welfare publication number 78-1526). The strength of this evidence is based on numerous sources, including 1) the experimental production of atherosclerotic lesions in animal fed diets that induce hypercholesterolemia, 2) knowledge of the nature and dynamics of the human atherosclerotic plaque, 3) the occurrence of hyperlipidemia in groups of subjects with clinically manifested atherosclerotic disease, 4) the study of ge-

| Summary of effects of various compounds on metabolism in fed hepatocytes | | | | | | |
|---|---|---|---|---|---|---|
| Compound | Dose (mM) | Fatty Acid Synthesis** | Cholesterol Synthesis** | Glucose Release** | Lactate*** | Pyruvate*** |
| No Addition | — | 0.024 ± 0.004 | 0.013 ± 0.002 | 0.787 ± 0.041 | 0.317 ± 0.095 | 0.186 ± 0.040 |
| Prior Art Compound* | 0.5 | 0.010 ± 0.002 | 0.010 ± 0.002 | 1.507 ± 0.047 | 0.383 ± 0.085 | 0.110 ± 0.013 |
| Example 10 | 0.5 | 0.003 ± 0.001 | 0.003 ± 0.001 | 1.357 ± 0.009 | 0.477 ± 0.084 | 0.220 ± 0.031 |
| Example 11 | 0.5 | 0.003 ± 0.001 | 0.002 ± 0.001 | 1.014 ± 0.099 | 0.437 ± 0.104 | 0.202 ± 0.028 |
| Example 14 | 0.5 | 0.003 ± 0.001 | 0.004 ± 0.001 | 1.492 ± 0.051 | 0.400 ± 0.091 | 0.185 ± 0.042 |

*Compound disclosed in U.S. Pat. No. 4,645,858. Example 19 (3-hydroxy-3-[12,12-dimethyltridecyl]glutaric acid)
**mmoles/min/gm wet weight
***mmoles/ml incubation medium With increased interest in the prevention of coronary heart disease and the recognition of the role of hyperlipoproteinemia as a risk factor, the search has been on to increase the number of drugs available for the treatment of hyperlipidemia. Treatment of the patient with hyperlipidemia has become more precise as knowledge of lipid metabolism and of the mechanism of action of hypolipidemic drugs has increased. The routine clinical measurement of the concentrations of cholesterol and triglycerides in plasma, which has become widespread, from its identification of patients with asymptomatic hyperlipidemia and has allowed recognition of the association of hyperlipidemia with such conditions as abdominal pain, pancreatitis, xanthomatosis, and premature vascular disease. These factors have emphasized the need for means to manage hyperlipidemia in the safest and simplest manner.

Hyperlipidemia is a sign of a heterogeneous group of diseases that differ in etiology, clinical manifestations, prognosis, and response to therapy. Understanding of the various hypolipidemias requires knowledge of the different types of lipoproteins that circulate in plasma, since it is in association with these proteins that nearly all lipids in plasma (except free fatty acids) are found. The major plasma lipids, including cholesterol and tryglycerides, do not circulate freely in solution, but rather are transported in blood in the form of complexes with lipoproteins. The major families of lipoproteins are the chylomicrons, very low density lipoproteins (VLDL), interimmediate density lipoproteins (IDL), low density lipoproteins (LDL), and high density lipoproteins (HDL). Thus, the measurement of total cholesterol and triglyceride concentrations in plasma is inadequate for diagnosis and as a guide to therapy, since reciprocal changes in the concentration of different classes of lipoproteins may mask the presence of an abnormality of an individual type of lipoprotein. The various disorders are classified in terms of specific types of lipoproteins netic hyperlipidemia that is associated with premature coronary heart disease, and 5) epidemiological studies of populations with different concentrations of cholesterol in plasma.

Concentrations of LDL in plasma correlate closely with the concentrations of cholesterol, since 60 to 75% of the total cholesterol in plasma is normally transported in association with this lipoprotein. Thus, concentrations of LDL or cholesterol carry more or less the same predictive power for assessment of risk of coronary heart disease.

The following non-limiting examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Melting points were determined on a Thomas-Hoover Unimelt capillary apparatus and are not corrected. Unless otherwise noted, IR and NMR spectra, taken over $CHCl_3$, were consistent with the assigned structure. The latter were recorded at 60 MHz with chemical shifts expressed in parts per million down field from the internal standard $(CH_3)_4Si$.

EXAMPLE 1

10-Carboxydecyl triphenylphosphonium bromide

A solution of 303 g (1.14 mol) of 11-bromoundecanoic acid and 303 g (1.16 mol) of triphenylphosphine in 3L of toluene was stirred and refluxed under $N_2$ for three days, then cooled to 0°. The crystalline solid was broken up, filtered off, washed with toluene and with ether, and then dissolved in a minimum of $CH_2Cl_2$. This solution was diluted with stirring to 4L with ether, the white crystalline powder was filtered off and dried at 40°/1 ml; 524 g (87%), mp 95°–98°. Calculated for $C_{29}H_{36}BrO_2P$ C, 66.03; H, 6 88. Found: C,66.36; H, 6.95.

EXAMPLE 2

3,3-Dimethoxy-2,2-dimethylpropanol

A solution of 24.4 g (0.24 mol) of 3-hydroxy-2,2-dimethylpropanal (Aldrich), 26 q (0.25 mol) of trimethyl orthoformate, and 0.5 mL of 6.8 N HCl/dioxane in 300 mL of methanol was allowed to stand at room temperature overnight. A slight excess of $NaOCH_3$ was added and the solvent evaporated at reduced pressure. The residue was dissolved in ether and the mixture filtered. After evaporation of solvent and fractionation twice through a 15 cm Vigreux column, the product was obtained as a water-white oil, bp 43–°48°/0.2mm, 18.5q (52%).

Calculated for $C_7H_{16}O_3$: C, 56.73; H, 10.88. Found: C, 56.79; H, 10.78.

EXAMPLE 3

3.3-Dimethoxy-2,2-dimethylpropanal

A suspension of 90g (0.61mol) of the product of Example 2 and 250mg (0 66 mol) of pyridinium dichromate was stirred rapidly in 2L of $CH_2Cl_2$ for 40 hours. The mixture was filtered through Celite, the filtrate passed through a column of Florisil and the solvent evaporated. Distillation of the residue through a 45cm vigreux column furnished the title compound as a water-white oil, bp 65°–68°/10mm, 31.4q (35%). Calculated for $C_7H_{14}O_3$: C,57.51; H, 9 65. Found: C, 57.69; H, 9.85.

EXAMPLE 4

Methyl 14,14-dimethoxy 13,13-dimethyl-11-tetradecenoate.

A mixture of 10.5gm (0.42mol) of NaH (as a 50% suspension in mineral oil) and 400 mL of dimethylsulfoxide (DMSO) was stirred and heated at 60° under nitrogen until the evolution of gas ceased, then cooled to and maintained at 20° to 25° while adding dropwise a solution of 111.0q (0.21 mol) of the product in Example 1 in 200 mL of DMSO. When this addition was complete, 600 mL of tetrahydrofuran (THF) was added and the suspension was cooled to 0° to 5° centigrade. A solution of 43.8g (0.30mol) of the product of Example 3 in 200 mL of THF was added over two minutes and the mixture was stirred rapidly and allowed to warm to room temperature overnight. Methyl iodide, 15.2q (0.25mol) was added, the mixture stirred for 8 hours, then an equal quantity of methyl iodide was added and stirring continued for 60 hrs. After adding 30 mL of MeOH and 20q of $K_2CO_3$ the lower-boiling solvents were evaporated at reduced pressure, and the remaining DMSO-solution was diluted with water and extracted with ether. This extract was washed well with water, dried ($K_2CO_3$), concentrated to 1L, and cooled. The white cystals that separated were filtered off and dried: 27.6g, mp 155°–156°: triphenylphosphine oxide. The filtrate was evaporated, the residue stirred with 2L of pentane, and an additional 13.4q of the oxide was filtered off. After evaporation of the solvent, the residue was flash chromatographed twice on 10 ×30 cm columns of silica gel in $CH_2Cl_2$. Distillation of the appropriate combined fractions furnished the title compound as a water-white oil bp 151°–156°/0.2 mm, 38.7q (56%).

Calculated for $C_{19}H_{36}O_4$: C, 69.47; H, 11 05. Found: C, 69.54; H, 11.20.

EXAMPLE 5

Methyl 14,14-dimethoxy 13,13-dimethyltetradecanoate

A solution of 38.7q (0 12mol) of the product of Example- 4 in THF was reduced with $H_2$ at 60 psi using 5% Pd on C at 25°. After filtering off the catalyst, the solvent was evaporated, the residue dissolved in pentane, and again filtered and evaporated Distillation of the residue furnished the title compound as a water-white oil, bp 153° to 168° 0.1 mm, 38.0g (98%). Calculated for $C_{19}H_{38}O_4$: C, 69.03; H, 11.59. Found: C, 69.30; H, 11.84.

EXAMPLE 6

17.17-Dimethoxy-16,16-dimethyl-4-allyl-4-hydroxyheptadecene-1

A crystal of iodine, 1 ml of commercial allyl magnesium bromide in ether and 0 5 g of allylbromide were added to a stirred suspension of 6.35 g (0.26 mol, 15% excess) of Mg turnings in 800 mL of dry THF at reflux. When the yellow color cleared, a solution of 31.6 g (0.26 mol) of allylbromide and 37.5 g (0.113 mol) of the product of Example 5 in 200 mL of THF was added dropwise in 45 minutes. After heating for an additional hour, the solution was cooled then decomposed with 10 ml of methanol. After dilution with ether, sufficient saturated $NH_4Cl$ solution was added to dissolve the Mg salts, the organic layer was separated, washed with saturated NaCl solution, dried ($K_2CO_3$), and evaporated at reduced pressure to give the product as a yellow oil, 43.8 g which was sufficiently pure for the subsequent step.

A 0.5 g portion of this material was distilled in a short-path apparatus at 0.1 mm, bath 170°–190°, with little loss to yield a water-white oil.

Calculated for $C_{24}H_{46}O_3$: C, 75.34; H, 12 12. Found: C, 75.66; H, 12.35.

EXAMPLE 7

14-Allyl-14-hydroxy-2,2-dimethyl-16-heptadecenal

A solution of 43.3 g (0.113 mol) of undistilled product of Example 6, 50 mL of $H_2O$, and 10 mL of 2.7N HCl (0.027 mol) in 500 mL of acetone was allowed to stand under $N_2$ for 20 hours; TLC (20% $C_2H_5OCOCH_3$-$CH_2Cl_2$) showed no more product of Example 6 Solid $K_2CO_3$, 2.8 g (0.020 mol), was added and the solution stirred for one hour. After dilution with 75 mL of $H_2O$ and 425 mL of acetone, 18.1 g (0.114 mol) of $KMnO_4$ was added and the mixture stirred rapidly for 4 hours until the pink color was gone, then filtered and the acetone evaporated at reduced pressure. The remaining aqueous solution was brought to pH 2 with dilute HCl and extracted with ether, which was washed once with dilute HCl and then extracted twice with dilute NaOH. The ether layer was dried ($K_2CO_3$), evaporated, the light-yellow oil dried at 30°/0.5 mm: producing 20.7 g (54%) of the title compound.

EXAMPLE 8

1 14-Allyl-14-hydroxy-2,2-dimethyl-16-heptadecenoic acid

The NaOH extracts from the product of Example 7 were brought to pH 2 with dilute HCl and extracted with ether. These extracts were dried ($Na_2SO_4$), evaporated and the yellow glass dried at 30° centigrade/0.5 mm. yielding 18.4 g (46%) of the title compound. A 0 28 g-sample prepared in this manner was flash chromatographed on a 1×15 cm column of silica gel in 20% $C_2H_5OCOCH_3$—$CH_2Cl_2$ and furnished 0.13 g of the title compound.

Calculated for $C_{22}H_{40}O_3$: C, 74.95; H, 11.44. Found: C, 74.13; H, 11.11.

EXAMPLE 9

Methyl 14-allyl-14-hydroxy-2,2-dimethyl-16-heptadecenoate

A cooled ether solution of 2.4 g of the product of Example 8 was added to excess $CH_2N_2$ in ether at 0° to 5°; after standing 2 hours, the excess $CH_2N_2$ was decomposed with dilute HCl. The ether layer was washed with $H_2O$, with dilute $NaHCO_3$, dried ($K_2CO_3$) and evaporated. The residue, 2.5 g, was flash chromatographed on a 10×20 cm column of silica gel in 20% $C_2H_5OCOCH_3$—$CH_2Cl_2$; a single fraction of 0.37 g was used for; a total of 1.35 g of title compound was obtained as a light yellow oil.

Calculated for $C_{23}H_{42}O_3$: C, 75.36; H, 11.55. Found: C, 74.86; H, 11.47.

EXAMPLE 10

3-(12-Carbomethoxy-12-methyl-tridecyl)-3-hydroxyglutaric acid

Ozone/$O_2$ was bubbled into a solution of (2 0 g 5.46 mmol) of the product of Example 9 and 4 mL of $CH_3COOH$ in 100 mL of $CH_2Cl_2$ at −70° until the blue color persisted, then $O_2$ was continued until clear. After adding 4 mL of $CH_3COOH$, the $CH_2Cl_2$ was removed at reduced pressure and 10 mL of $CH_3COOH$, 8 mL of $H_2O$, 5 mL of 10% $H_2SO_4$ and 5 mL of 30% $H_2O_2$ were added.

This mixture was heated at 70°–75° for one hour until clear, then diluted with $H_2O$ and extracted with ether. The ether was washed well with dilute HCl (until the starch-iodide test for peroxide was negative) then extracted with dilute NaOH This basic solution was brought to pH 2 with dilute HCl, then extracted with ether which was dried and evaporated; the yellow glass was dried at 30°/0.5 mm: this produced 1.90 g (86%) of title compound.

Calculated for $C_{21}H_{38}O_7$: C, 62.66; H, 9 52 Found: C, 63.00; H, 9.88.

EXAMPLE 11

3-(12-Carboxy-12-methyl-tridecyl)-3-hydroxyglutaric acid

A 0.90 g sample of the product of Example 10 dissolved in 10 mL of 10% NaOH was heated at 50° overnight. The solution was made pH 2 with dilute HCl and extracted with ether which was dried ($NH_2SO_4$) and evaporated. The residue dissolved and $CH_2Cl_2$ was filtered, evaporated and dried at 30°/0.5 mm to give the title compound as a yellow glass, 0.90 g. A portion crystallized twice from ether pentane gave the title compound as tiny white clusters, m. 56°–58°.

Calculated for C20H3607 C, 61.83; H, 9.34. Found: C, 61 83; H, 9.45.

EXAMPLE 12

Dimethyl -(12-carbomethoxy-12-methyl-tridecyl)-3-hydroxyglutarate

A 1.65 g sample of the product of Example 11 was esterified with $CH_2N_2$ as described for Example 9; the product was flash chromatographed on a 5×25 cm column of silica gel in 5% ether-$CH_2Cl_2$ yielding a yellow oil 0.65 g, of title product.

Calculated for $C_{23}H_{42}O_7$: C, 64.15; H, 9 83. Found: C, 64.55; H, 9.69.

EXAMPLE 13

14-Allyl-14-hydroxy-2,2-dimethyl-16-heptadecen-1-ol

A solution of 1.01 g (3.0 mmol) of the title compound of Example 7 and 2.5 g (10 mmol) of lithium tris-t-butoxyaluminum hydride in 250 mL of tetrahydrofuran under $N_2$ was stirred overnight at room temperature. After dilution with ether the mixture was washed sequentially with saturated solutions of Na-K tartrate, NaCl, then dried and the solvents removed. The residue was dissolved in 100 mL of Skellysolve A, decolorized with activated charcoal, the mixture filtered and the filtrate evaporated. The residue was dried at 40°/3 mm to yield 0.92 g of a cloudy oil.

EXAMPLE 14

3 (13-Hydroxy-12,12-dimethyl-tridecyl)-3-hydroxyglutaric acid

Ozonization and oxidation of 0.80 g of the product of Example 13 prepared above using the conditions for the preparation of the product in Example 10 furnished 0.73 g of a yellow glass. Upon crystallization twice from 1:1 ether-hexane the title compound was obtained as a white crystalline powder, 0.30q, mp 102°–3°.

Calculated for $C_2OH_{38}O_6$: C, 64.14; H, 10.23. Found: C, 64.18; H, 10.41.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal treated, severity of hyperlipidemia, dosage related adverse effects, if any, observed and analogous considerations. Likewise, the specific pharmacological responses observed may vary according to and depending upon the particular active compound selected or whether different active compounds are used in combination or in the presence of suitable pharmaceutical carriers, as well as the type of formulation and mode of administration employed, and such expected variations or differences in the results are contemplated in accordance with the objects and practices of the present invention. It is intended therefore that the invention be limited only by the scope of the claims which follow, and that such claims be interpreted as broadly as is reasonable.

What is claimed is:

1. A compound of the general formula

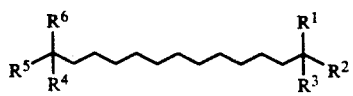

and the pharmaceutically acceptable salts thereof, wherein $R^1$ is hydroxy and $R^6$ is independently $$-(CH_2)_n-O-H,$$

-continued

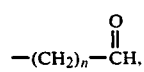

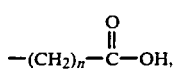

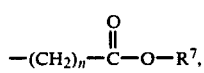

wherein $R^7$ is alkyl of from 1 to 10 carbon atoms, and n is an independent integer of from 0 to 10; wherein $R^2$ and $R^3$ are alkyl or alkenyl of from 1 to 5 carbon atoms; and wherein $R^4$ and $R^5$ are independently alkyl of from 1 to 10 carbon atoms.

2. The compound as claimed in claim 1, wherein $R^2$ and $R^3$ are both —CH$_2$—CH=CH$_2$.

3. The compound as claimed in claim 1, wherein $R^4$ and $R^5$ are both —CH$_3$.

4. The compound as claimed in claim 1, wherein $R^1$ is —OH and $R^6$ is —CO$_2$CH$_3$.

5. A compound of the general formula

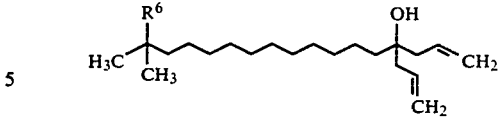

and the pharmaceutically acceptable salts thereof, wherein $R^6$ is —CH$_2$—OH, —OH,

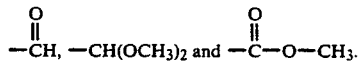

6. The compound as claimed in claim 5, which is methyl 14-hydroxy-2,2-dimethyl-14-(2-propenyl)-16-heptadecenoate.

7. The compound as claimed in claim 5, which is 14-hydroxy-2,2-dimethyl-14-(2-propenyl)-16-heptadecenal.

8. The compound as claimed in claim 5, which is 14-hydroxy-2,2-dimethyl-14-(2-propenyl)-16-heptadecenoic acid.

9. The compound as claimed in claim 5, which is 2,2-dimethyl-14-(2-propenyl)-16-heptadecene-1,14-diol.

* * * * *

UNITED STATES PATENT AND TRADEMARK OFFICE
CERTIFICATE OF CORRECTION

PATENT NO. : 5,233,063

DATED : August 3, 1993

INVENTOR(S) : Baran, et al.

Page 1 of 5

It is certified that error appears in the above-indentified patent and that said Letters Patent is hereby corrected as shown below:

Column 1, line 30, reading "hyperlipoproteinemia" should read -- hyperlipoproteinemia, --.

Column 2, line 20, reading "wherein $R^1$" should read -- wherein $R^7$ --.

Column 3, line 20, reading "ar those" should read -- are those --.

Column 6, line 9, reading "available startinq" should read -- available starting --.

Column 7, line 53, reading "the type." should read -- the type, --.

Column 8, line 26, reading "8-lactose," should read -- $\beta$-lactose, --.

Column 8, line 46, reading "8:00 p m" should read -- 8:00 p.m. --.

Column 8, line 68, reading "for glycogen." should read -- for glycogen, --.

Column 9, line 1, reading "369 379)" should read -- 369-379) --.

UNITED STATES PATENT AND TRADEMARK OFFICE
CERTIFICATE OF CORRECTION

PATENT NO. : 5,233,063
DATED : August 3, 1993
INVENTOR(S) : Baran, et al.

It is certified that error appears in the above-indentified patent and that said Letters Patent is hereby corrected as shown below:

Column 9, line 6, reading "equivalents/q" should read -- equivalents/g --.

Column 9, line 15, reading "time The" should read -- time. The --.

Column 9, line 48, reading "heterogeneous" should read -- heterogenous --.

Column 11, line 7, reading "26 q" should read -- 26 g --.

Column 11, line 16, reading "18.5 q" should read -- 18.5 g --.

Column 11, line 22, reading "3.3-Dimethoxy-" should read -- 3,3-Dimethoxy- --.

Column 11, line 24, reading "(0 66 mol)" should read -- (0.66 mol) --.

Column 11, line 30, reading "31.4 q" should read -- 31.4 g --.

Column 11, line 31, reading "9 65." should read -- 9.65. --.

Column 11, line 34, reading "dimethoxy" should read -- dimethoxy- --.

UNITED STATES PATENT AND TRADEMARK OFFICE
CERTIFICATE OF CORRECTION

PATENT NO. : 5,233,063
DATED : August 3, 1993
INVENTOR(S) : Baran, et al.

It is certified that error appears in the above-indentified patent and that said Letters Patent is hereby corrected as shown below:

Column 11, line 41, reading "111.0 q" should read -- 111.0 g --.

Column 11, line 49, reading "15.2 q" should read -- 15.2 g --.

Column 11, line 53, reading "20 q" should read -- 20 g --.

Column 11, line 61, reading "13.4 q" should read -- 13.4 g --.

Column 11, line 66, reading "38.7 q" should read -- 38.7 g --.

Column 11, line 67, reading "11 05." should read -- 11.05 g --.

Column 12, line 3, reading "dimethoxy 13" should read -- dimethoxy-13 --.

Column 12, line 4, reading "38.7 q (0 12 mol)" should read -- 38.7 g (0.12 mol) --.

Column 12, line 4, reading "Example- 4" should read -- Example 4 --.

Column 12, line 8, reading "evaporated Distillation" should read -- evaporated. Distillation --.

Column 12, line 15, reading "17 17-" should read -- 17,17- --.

UNITED STATES PATENT AND TRADEMARK OFFICE
CERTIFICATE OF CORRECTION

PATENT NO. : 5,233,063
DATED : August 3, 1993
INVENTOR(S) : Baran, et al.

It is certified that error appears in the above-indentified patent and that said Letters Patent is hereby corrected as shown below:

Column 12, line 18, reading "0 5 g" should read -- 0.5 g --.

Column 12, line 36, reading "12 12." should read -- 12.12. --.

Column 12, line 46, reading " 6 Solid" should read -- 6. Solid --.

Column 12, line 60, reading "1 14-" should read -- 14- --.

Column 12, line 67, reading "mm. yielding" should read -- mm, yielding --.

Column 12, line 67, reading "A 0 28" should read -- A 0.28 --.

Column 13, line 26, reading "(2 0 g" should read -- (2.0 g --.

Column 13, line 38, reading "NaOH" should read -- NaOH. --.

Column 13, line 43, reading "H, 9 52" should read -- H, 9.52 --.

Column 13, line 59, reading "C20H36O7" should read -- $C_{20}H_{36}O_7$: --.

Column 13, line 60, reading "C, 61 83;" should read -- C, 61.83; --.

Column 13, line 64, reading "-(12-carbomethoxy-" should read -- 3-(12-carbomethoxy --.

UNITED STATES PATENT AND TRADEMARK OFFICE
CERTIFICATE OF CORRECTION

PATENT NO. : 5,233,063
DATED : August 3, 1993
INVENTOR(S) : Baran, et al.

It is certified that error appears in the above-indentified patent and that said Letters Patent is hereby corrected as shown below:

Column 14, line 3, reading "H, 9 83." should read -- H, 9.83. --.

Column 14, line 22, reading " (13-" should read -- 3-(13- --.

Column 14, line 30, reading "0.30 q," should read -- 0.30 g, --.

Signed and Sealed this

Twenty-first Day of March, 1995

Attest:

BRUCE LEHMAN

Attesting Officer

Commissioner of Patents and Trademarks